US011554048B2

(12) United States Patent
Sullivan et al.

(10) Patent No.: US 11,554,048 B2
(45) Date of Patent: Jan. 17, 2023

(54) SYSTEM AND METHOD FOR TREATING MEIBOMIAN GLAND DYSFUNCTION

(71) Applicant: The Schepens Eye Research Institute, Inc., Boston, MA (US)

(72) Inventors: David A. Sullivan, Boston, MA (US); Yang Liu, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 467 days.

(21) Appl. No.: 16/289,195

(22) Filed: Feb. 28, 2019

(65) Prior Publication Data

US 2019/0269553 A1 Sep. 5, 2019

Related U.S. Application Data

(60) Provisional application No. 62/637,984, filed on Mar. 2, 2018.

(51) Int. Cl.
*A61F 9/007* (2006.01)
*A61F 9/009* (2006.01)
(Continued)

(52) U.S. Cl.
CPC .......... *A61F 9/009* (2013.01); *A61F 9/00772* (2013.01); *A61F 9/04* (2013.01);
(Continued)

(58) Field of Classification Search
CPC ........ A61F 9/009; A61F 9/00772; A61F 9/04; A61F 2009/00885; A61F 2009/00897; A61H 35/02; A61B 3/101
See application file for complete search history.

(56) References Cited

U.S. PATENT DOCUMENTS

2003/0004556 A1\* 1/2003 McDaniel ................ A61K 8/67
607/88
2008/0114424 A1 5/2008 Grenon et al.
(Continued)

FOREIGN PATENT DOCUMENTS

CA 2831095 C 12/2015

OTHER PUBLICATIONS

Qiao et al. (Sep. 1, 2013) "Emerging Treatment Options for Meibomian Gland Dysfunction", Clinical Ophthalmology, 7:1797-1803.

*Primary Examiner* — Ankit D Tejani
*Assistant Examiner* — Joshua Brendon Solomon
(74) *Attorney, Agent, or Firm* — Fish & Richardson P.C.

(57) ABSTRACT

Systems and methods of treating meibomian and sebaceous gland dysfunction. The methods include reducing oxygen concentration in the environment of one or more dysfunctional meibomian and sebaceous glands, thereby restoring a hypoxic status of one or more dysfunctional meibomian and sebaceous glands. The reducing of the oxygen concentration is accomplished by restricting blood flow to the one or more dysfunctional meibomian and sebaceous glands and the environment of one or more dysfunctional meibomian sebaceous glands. The restricting of the blood flow is accomplished by contracting or closing one or more blood vessels around the one or more dysfunctional meibomian or sebaceous glands. The methods also include giving local or systemic drugs that lead to the generation of hypoxia-inducible factors in one or more dysfunctional meibomian and sebaceous glands.

10 Claims, 2 Drawing Sheets

(51) Int. Cl.
 *A61H 35/02* (2006.01)
 *A61F 9/04* (2006.01)
 A61F 9/008 (2006.01)
 A61B 3/10 (2006.01)

(52) U.S. Cl.
 CPC .............. *A61H 35/02* (2013.01); *A61B 3/101* (2013.01); *A61F 2009/00885* (2013.01); *A61F 2009/00897* (2013.01)

(56) References Cited

U.S. PATENT DOCUMENTS

| | | |
|---|---|---|
| 2009/0182231 A1 | 7/2009 | Barthe et al. |
| 2009/0318422 A1 | 12/2009 | Isowaki et al. |
| 2012/0003296 A1* | 1/2012 | Shantha ............... A61K 39/395 424/450 |
| 2014/0186309 A1* | 7/2014 | Klassen ............... A61K 9/0048 435/378 |
| 2015/0141328 A1 | 5/2015 | Sullivan et al. |
| 2016/0030726 A1 | 2/2016 | Hwang et al. |
| 2017/0165105 A1 | 6/2017 | Anderson et al. |
| 2019/0015444 A1* | 1/2019 | Mootha ............... A61K 31/4745 |
| 2020/0138669 A1* | 5/2020 | Berdahl ............... A61M 16/16 |

* cited by examiner

SYSTEM AND METHOD FOR TREATING MEIBOMIAN GLAND DYSFUNCTION

PRIORITY INFORMATION

The present application claims priority to U.S. Provisional Patent Application No. 62/637,984, filed Mar. 2, 2018, the content of which is incorporated herein by reference in its entirety.

FIELD OF THE DISCLOSURE

The present disclosure generally relates to methods for treatment of various dysfunctions such as a meibomian gland dysfunction (MGD) and a sebaceous gland dysfunction (SGD). Methods are disclosed for treating dry eye disease as well.

BACKGROUND

The preocular tear film is extremely important for maintaining ocular surface integrity, protecting against microbial challenge and preserving visual acuityl-4. These functions, in turn, are critically dependent upon the composition and stability of the tear film structure, which includes an underlying mucin foundation (predominantly from goblet cells and conjunctival and corneal epithelial cells), a middle aqueous component (primarily from lacrimal gland epithelial cells) and an overlying lipid layer (secreted by meibomian gland [MG] epithelial cells). Disruption, deficiency or absence of the tear film may severely impact the eye: these disorders may lead to desiccation of the ocular surface, ulceration of the cornea, an increased susceptibility to infection and visual defects.

Throughout the world countless individuals suffer from tear film dysfunctions, which are collectively diagnosed as dry eye disease (DED). DED is generally characterized by a vicious cycle of tear film hyperosmolarity and instability and ocular surface stress, leading to increased friction, inflammation, eye damage and visual impairment. DED afflicts countless people throughout the world (i.e., greater than 40 million in the USA), and is one of the most frequent causes of patient visits to eye care practitioners. Moderate to severe DED is associated with significant pain, role limitations, low vitality and poor general health. The burden of DED for the USA healthcare system is estimated to be over $3.8 billion, and, because of diminished productivity, $55.4 billion for the USA overall.

The leading cause of DED is MGD). In fact, a recent study found that over 85% of clinically-identified DED patients exhibited signs of MGD. Normally, MGs produce abundant lipids (e.g. cholesterol and phospholipids), that accumulate in lysosomes, are secreted in a holocrine manner into lateral ducts, and are ultimately released onto the ocular surface. This lipid secretion (i.e. meibum) provides a clear optical surface for the cornea, interferes with bacterial colonization, and retards tear overflow. Meibum also promotes the stability and prevent the evaporation of the tear film, thereby playing an essential role in the health of the ocular surface.

However, MGD, and the resulting meibum insufficiency, destabilize the tear film, and increase its osmolarity and evaporation. The most common cause of human MGD is excretory duct obstruction, due to reduced meibum quality and hyperkeratinization of the terminal duct epithelium. This obstruction, which often occurs during aging, androgen deficiency and 13-cis retinoic acid (RA) use, may lead to cystic dilatation of glandular ducts, atrophy and loss of MG epithelial cells (MGECs) and MG dropout. There is no global cure for MGD. There is also no known way to regenerate MGs after dropout.

SUMMARY

Various treatment systems and methods are disclosed for treating several dysfunctions. For example, a method of treating MGD is disclosed. The methods include reducing oxygen concentration in an eyelid environment of one or more dysfunctional MGs, as well giving local or systemic drugs that lead to the generation of hypoxia-inducible factors (HIFs) in one or more dysfunctional MGs. These HIFs are induced by relative hypoxia and promote the function of MGs. The eyelid includes the skin and tarsal tissues between the eyebrow and the lower margin of the orbital cavity, and the MGs are located in the lower and upper eyelids. The blood supply for the eyelids are formed by anastomoses of the lateral palpebral arteries and medial palpebral arteries, branching off from the lacrimal artery and ophthalmic artery, respectively.

There are different definitions for hypoxia. The terms physiological, modest, moderate and severe hypoxia and anoxia have been used to designate 10-14, 2.5, 0.5, 0.1 and 0% O2, respectively. We use the terminology "relative hypoxia," because we have discovered that MGs exist in an environment containing oxygen levels below 1.3%. This low partial pressure of oxygen ($pO_2$) is "normoxic" or "physioxic" for MGs. For the purposes of this application, we characterize this normoxic/physioxic environment of the MGs as "relatively hypoxic."

A benefit of these treatments is that they restore a relatively hypoxic status or activate hypoxia-inducible factors in one or more dysfunctional MGs. Reducing of the oxygen concentration can be accomplished by restricting blood flow to the one or more dysfunctional MGs and the eyelid environment of one or more dysfunctional MGs. The effects of reduced oxygen concentration can also be elicited by the systemic or local use of agents that induce the generation of HIFs in the dysfunctional MGs. The action of these agents essentially mimics the effects of low $pO_2$.

Restricting of the blood flow can be accomplished in a number of ways, including by contracting or closing one or more blood vessels around the one or more dysfunctional MGs. For example, restricting the blood flow can be achieved, among other approaches, using one or more of a 532-nm potassium titanyl phosphate (KTP) laser, a 532-nm neodymium yttrium-aluminum-garnet (Nd:YAG) laser, a 578-nm copper vapor laser, 585-600-nm pulsed dye laser (PDL), a dual 595-nm PDL, a long-pulse alexandrite (755 nm), a 800-983-nm diode laser, a 1,064-nm Nd:YAG laser, indocyanine green augmented laser therapy, PDL treatment combined with rapamycin, intense pulsed light (IPL), carbon dioxide ($CO_2$) laser, cryotherapy, vascular endothelial growth factor (VEGF)/vascular endothelial growth factor receptor (VEGFR) inhibitors or antagonists, systemic and/or local beta-blockers, anti-angiogenic molecules and mixtures thereof. Any of these devices can be configured specifically for this treatment. The hypoxic status can be induced in one or more of the following ways: pharmaceutically, surgically, using a laser, using an intense-pulsed light, with a device and/or using hypoxia chamber goggles.

The effects of reduced oxygen concentration can also be elicited by the systemic or local use of agents that induce the generation of HIFs in the dysfunctional MGs. These agents include such drugs as one or more of prolyl hydroxylases inhibitors, (i.e. FG-4592/roxadustat, FG-2216, daprodustat/GSK1278863, vadadustat/AKB-6548, molidustat/BAY 85-3934, desidustat/ZYAN1), Dimethyloxalylglycine (DMOG), desferrioxamine (DFX) and cobalt chloride (CoCl2), etc.

In another aspect of this disclosure, methods of treating dry eye disease are disclosed. The dry eye disease in one aspect occurs due to MGD. The methods include reducing oxygen concentration in an eyelid environment of one or more dysfunctional MGs, as well as using HIF-inducing agents for the treatment of one or more dysfunctional MGs. The methods restore a relatively hypoxic status of one or more dysfunctional MGs.

In another aspect, methods of improving a health of one or more MGs affected by MGD and reversing a dropout of the one or more MGs are disclosed. The methods include restoring a relatively hypoxic environment for one or more MGs by restricting blood flow and thereby reducing oxygen concentration in an eyelid environment of the one or more MGs, as well as by using HIF-inducing agents for the treatment of one or more dysfunctional MGs.

In yet another example, a method of treating sebaceous gland (SG) dysfunction is disclosed. The methods include reducing oxygen concentration in an environment in one or more dysfunctional SGs, as well as using HIF-inducing agents for the treatment of one or more dysfunctional SGs. These methods restore a hypoxic status of one or more dysfunctional SGs. The reducing of the oxygen concentration can be accomplished by restricting blood flow to the one or more dysfunctional SGs and the environment of the one or more dysfunctional SGs. The restricting of the blood flow can be accomplished by contracting or closing one or more blood vessels around the one or more dysfunctional SGs by using one or more of a pharmaceutical, surgery, a laser, an intense pulsed light, and a device. The effects of reduced oxygen concentration can also be elicited by the systemic or local use of agents that induce the generation of HIFs in the dysfunctional SGs.

Another aspect of this disclosure describes a method of treating hair loss. The hair loss can occur due to sebaceous gland dysfunction. The methods include reducing oxygen concentration in an environment in one or more dysfunctional SGs, as well as using HIF-inducing agents for the treatment of one or more dysfunctional SGs. These methods restore a hypoxic status of one or more dysfunctional SGs.

A further aspect of this disclosure is method of improving a health of one or more dysfunctional SGs. The method includes restoring a relatively hypoxic environment for the one or more dysfunctional SGs by restricting blood flow and thereby reducing an oxygen concentration in a local environment of one or more dysfunctional SGs, as well as by using HIF-inducing agents for the treatment of one or more dysfunctional SGs.

Yet another aspect of this disclosure relates to a method of promoting terminal differentiation of one or more MGs by reducing oxygen concentration in an eyelid environment of the one or more MGs or by using by using HIF-inducing agents for the treatment of one or more dysfunctional MGs. The terminal differentiation can be further enhanced by local ocular treatment with, and MG exposure to, phospholipidosis-inducing drugs.

BRIEF DESCRIPTION OF THE DRAWINGS

Various embodiments in accordance with the present disclosure with reference to the drawing, in which.

Figure 1:
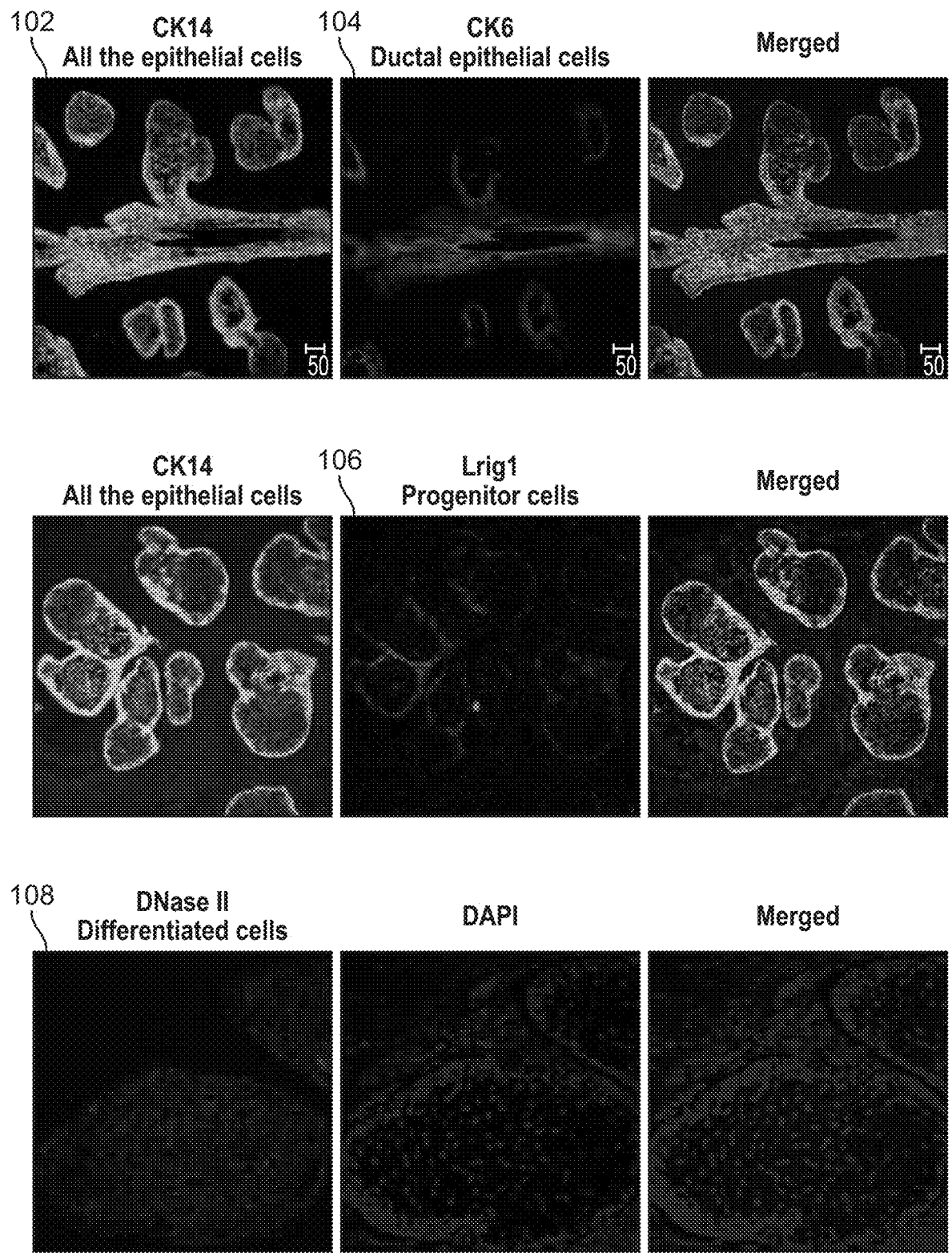
FIG. 1 is a depiction of various cells.

While the disclosed technology is described herein by way of example for several embodiments and illustrative drawings, those skilled in the art will recognize that the disclosed technology is not limited to the embodiments or drawings described herein. It should be understood that the drawings and detailed description thereto are not intended to limit embodiments to the particular form disclosed, but on the contrary, the intention is to cover all modifications, equivalents and alternatives falling within the spirit and scope as defined by the appended claims. As used throughout this application, the words "can" or "may" are used in a permissive sense (i.e., meaning having the potential to), rather than the mandatory sense (i.e., meaning must). Similarly, the words "include", "including", and "includes" mean including, but not limited to.

DETAILED DESCRIPTION

The conventional treatments of MGD are generally designed to enhance oxygen delivery to the affected tissue by increasing blood flow to and around the affected MGs and/or its local environment. For example, an accepted standard of care to alleviate MGD is to use eyelid heat therapies, which enhance oxygen delivery by increasing blood flow. Given that MG are lipid producing cells this therapeutic approach seems sensible considering that other lipid producing cells (i.e. adipocytes) in fat tissues require an abundant blood supply as the source of oxygen. Therefore an increase in circulation would deliver more oxygen to the tissues. The eyelid telangiectasia that often follows MGD could theoretically be a manifestation of the body's attempt to increase the local blood flow and oxygen supply to the MG and its environment.

In light of the forgoing, the present disclosure is, in part, based upon demonstrating that a relatively hypoxic environment is actually beneficial for the MG health. A further aspect of the present disclosure is to demonstrate that the loss of this hypoxic status plays a major role in MGD pathogenesis. Accordingly, an embodiment of the present disclosure discloses novel and effective methods for treatment of MGD based upon the restoration of the hypoxic environment surrounding the MG or inducing HIFs in the MG. Considering that a person of ordinary skill in the art would expect the lipid synthetic process to require considerable supply of oxygen, a therapeutic process based upon inducing a hypoxic MG environment or inducing HIFs in the MG for treatment of MGD, a condition associated with a degree of decreased lipid synthesis and gland atrophy, would seems counterintuitive.

Therefore, one embodiment of the present disclosure is directed towards establishing that a relatively hypoxic environment is beneficial for MG health and that the loss of this hypoxic status plays a major role in MGD pathogenesis. As such, one aspect of the present disclosure is directed towards an effective treatment for MGD and the regeneration of MGs that is based upon restoration of the hypoxic environment surrounding MG or by inducing HIFs in the MG.

MGs are relatively hypoxic. In addition, in experimental observations associated with the present disclosure, it has been identified that hypoxia promotes the maturation of immortalized human (IH) MGECs. More specifically, the experimental results reveal that both human and mouse MGs are relatively hypoxic tissues. This status has been demonstrated by staining relevant tissue samples with glucose transporter 1 and pimo, which are widely used hypoxia markers. The experimental findings extend observations made hitherto, that the environment of the MG is one of the most hypoxic areas in the human body.

Empirical observations conducted in connection with the disclosed disclosure demonstrate that the vasculature of both human and mouse MGs is situated beyond the basement membrane of MG acini. This distance, by Krogh's law, would decrease the amount of oxygen diffusing from blood vessels to the MGs and create a relatively hypoxic environment for the MG. This relative hypoxia makes sense, given that MG acinar epithelial cells accumulate lipids primarily in lysosomes, rather than the cytoplasm as in adipocytes, and hypoxia can lead to an up-regulation of genes that function in lysosome and lipid metabolism. Thus, it appears that MG epithelial cells do not require much oxygen to produce and release lipids. One consideration is that as MGECs mature, they move further away from the oxygen source and lose mitochondria. This process is quite different than found with other lipid producing cells (i.e. adipocytes). Another consideration is that acinar atrophy in MGD is associated with a thickening of the basement membrane. This anatomical development may represent a compensatory response to decrease oxygen delivery from adjacent vessels and to restore the relative hypoxia needed for optimal MG function. Most importantly, low oxygen concentrations have been found to allow stem cells to maintain their stemness, and may also be useful in maintaining and expanding a population of cells that is in limited supply. Such a process would be critical for MG regeneration after dropout in vivo.

In accordance to one aspect of the present disclosure, it has been demonstrated that low oxygen levels (1-10%) promote the differentiation of IHMGECs. This hypoxic effect is associated with a significant rise in the number and size of lysosomes, as well as increased DNase II activity and decreased Lamp-1 expression. These latter changes are consistent with heightened terminal differentiation and holocrine secretion. The hypoxic influence on terminal differentiation is further enhanced by combining low oxygen levels with iHMGEC exposure to phospholipidosis-inducing drugs, such as azithromycin (i.e. 10 µg/ml).

It has further been observed that low oxygen levels (3-10%) do not interfere with the proliferation of iHMGECs after approximately 5 days of exposure. Longer hypoxic exposure, as noted above, may leads to the terminal differentiation and loss of cells (i.e. due to holocrine secretion).

It has been found that roxadustat (20-100 µM), which is a representative of the HIF-inducing agents, activates the hypoxia pathway in IHMGECs by significantly increasing the level of HIF1α. Roxadustat significantly induces lipid production and terminal differentiation of the IHMGECs.

Empirical observations carried out in testing different aspects of the present disclosure indicate that the disclosed treatment strategies to create a hypoxic MG environment or treat with HIF-inducing agents may well serve as new and effective therapies for the treatment of MGD.

Example 1: Experiment Designed to Demonstrate that MG is Relatively Hypoxic for Physiological Reasons and that this Condition is Actually Beneficial for the MG In order to demonstrate the MG is relatively hypoxic for physiological reasons and that this condition is actually beneficial for the MGs, samples of human and mouse eyelid segments, and IHMGECs were studied. To evaluate oxygen levels in the mouse MG and vicinity, pimo (100 mg/kg) was intraperitoneally injected 2 hours before sacrifice. This compound is a common marker used in vivo to stain hypoxic tissues. Mouse eyelids were removed, processed for histology, and counterstained with hematoxylin to delineate lid anatomy. Resected human eyelid samples, obtained from healthy patients following their lid surgeries, were stained with the hypoxia markers, glucose transporter 1 (Glut-1), carbonic anhydrase 9 (CA9) and HIF1a. To determine the effect of low oxygen levels on IHMGECs, cells were cultured under proliferating and differentiating conditions in both normoxic (20% O2) and relatively hypoxic (5% O2) environments for 5 or 14 days. IHMGECs were evaluated for cell number, neutral lipid content (LipidTOX), lysosome accumulation (LysoTracker), and expression of different proteins (proliferating cell nuclear antigen [PCNA], HIF1a) by Western blots. Experiments were approved by an Institutional Review Board and an Institutional Animal Care and Use Committee.

The results of the experiment in Example 1 demonstrate that mouse MGs, and not adjacent tissue, feature intense staining for pimo. Similarly, it was discovered that human MGs, and not the surrounding tissue, show intense staining for Glut-1, CA9 and HIF1a. Relatively hypoxic conditions did not influence the proliferation of IHMGECs, but did appear to accelerate their differentiation.

The above stated results lead to conclusion that MGs exist in a relatively hypoxic environment. It is noteworthy to consider that in other tissues, low oxygen concentrations allow stem cells to maintain their stemness, which may also be true for MGs.

In summary the main aspects of the disclosed disclosure are directed to establishment of the importance of a hypoxic environment for MG health, demonstration that loss of this hypoxic status is associated with MGD, and that low oxygen therapy is an effective treatment for MGD, both in vivo and in vitro. Furthermore additional embodiment are directed to the determination of whether restoration of a hypoxic environment can reverse MG dropout.

Work done as part of the present disclosure has successfully identified, in human MGs, specific biomarkers for all the epithelial cells (i.e. Cytokeratin 14, K14), ductal epithelial cells (i.e., cytokeratin, K6), progenitor (i.e., Lrig 1), and differentiated cell (i.e. DNase II) as respectively indicated by labels 102, 104, 106 and 108 in FIG. 1. These biomarkers will not only enable a clear identification of the anatomy and the structure of the MGs, but also the determination of the effect of oxygen tensions on various parts of the MG.

Figure 2:
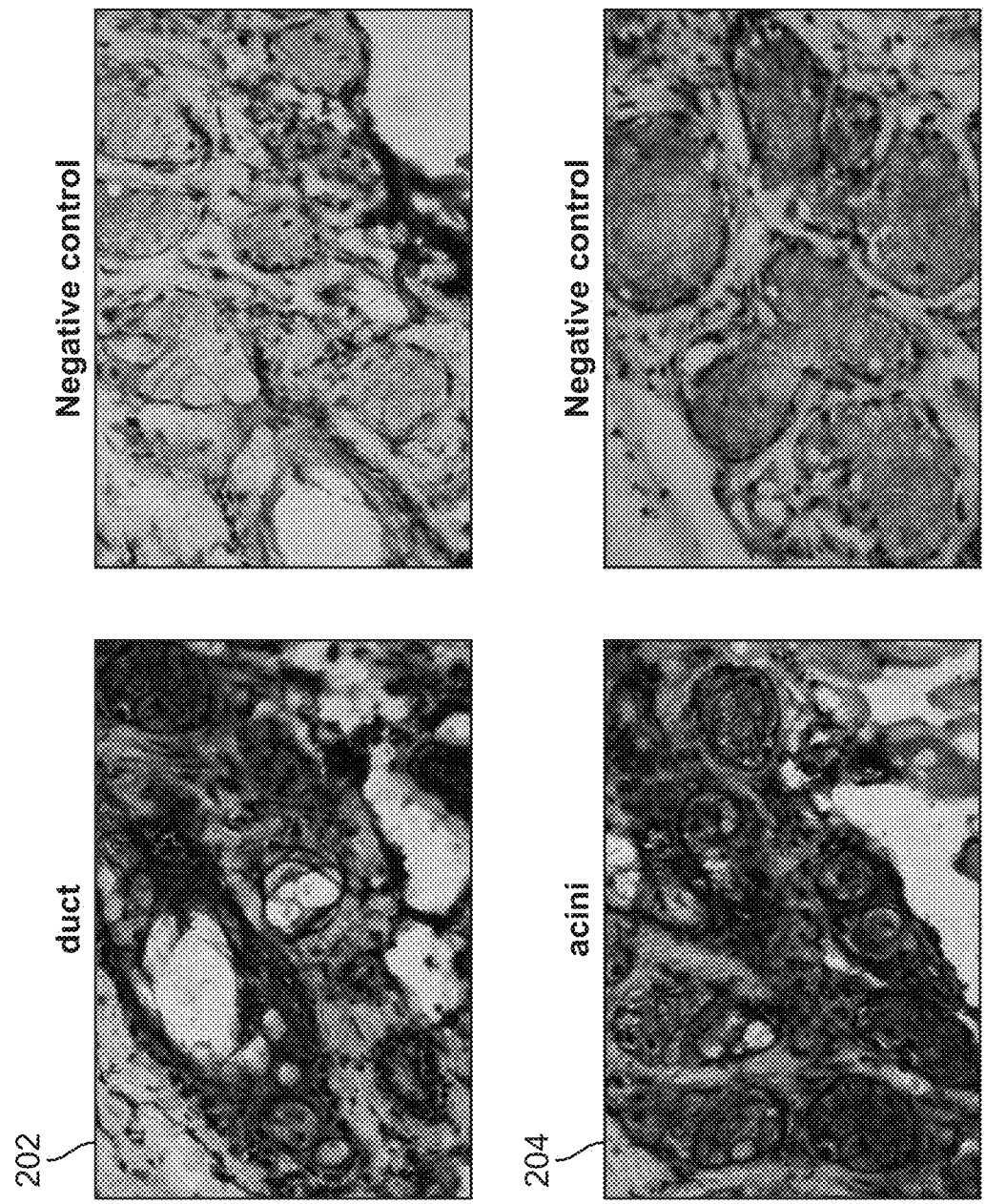
FIG. 2 is a graphical representation of staining of pimonidazole hydrochloride (pimo) in MG duct and acini of healthy mice.

Photomicrograph 202 and 204 depicted in FIG. 2 respectively demonstrates the strong staining of pimo in MG duct and acini of healthy WT mice. This confirms the physiological hypoxic status of the tissue. The staining patterns of pimo and Glut-1 are similar in mouse tissue.

One aspect of the present disclosure seeks to confirm that healthy MGs exist in a relatively hypoxic environment, and that loss of this hypoxic status is associated with MGD. While another aspect of the disclosure will demonstrate that restoration of this hypoxic environment or inducing HIFs in the MG serve as an effective treatment for MGD in vivo and in vitro. For comparison, a recent study shows that hypoxia can induce heart regeneration and reverse neurodegeneration in adult mice.

As MGD is considered to be the leading cause of DED one embodiment of the disclosed method may be utilized in treating DED occurring due to MGD. This would entail reducing oxygen concentration in an eyelid environment of one or more dysfunctional MGs, thereby restoring a hypoxic status of the eyelid environment of or inducing HIFs in one or more dysfunctional MGs.

In accordance to another embodiment, the disclosed disclosure may be directed to improving a health of one or more glands in general and in one example to MGs affected by MGD and reversing a dropout of the one or more MGs. This desirable outcome may be achieved by restoring a relatively hypoxic environment for the one or more MGs by reducing oxygen concentration in an eyelid environment of the one or more MGs, or inducing HIFs in the MG as described earlier. The action of reducing the oxygen concentration may be accomplished, for example, by restricting blood flow to and around the one or more affected MGs, as well by giving local or systemic drugs that lead to the generation of HIFs in one or more dysfunctional MGs.

It should be noted that the work described in connection with MG and treatment of MGD and disclosed as part of the present disclosure also applies to SGs in general. The methods can be applied to any gland and particularly for the glands disclosed. As such further embodiments of the present disclosure demonstrate that a relatively hypoxic environment is beneficial for SG health, and that: [a] loss of this hypoxic status contributes to SG dysfunction, hair follicle damage and hair loss; and [b] restoration of this hypoxic SG environment or inducing HIFs in the SG will serve as effective treatments to ameliorate SG dysfunction and to prevent hair follicle damage and hair loss.

As such, another embodiment of the present disclosure is directed to treatment of sebaceous gland dysfunction (SGD), by reducing oxygen concentration in an environment of one or more dysfunctional SGs, thereby restoring a hypoxic status of the environment of the one or more dysfunctional SGs, as well by giving local or systemic drugs that lead to the generation of HIFs in one or more dysfunctional SGs.

The reducing of the oxygen concentration in an environment of one or more dysfunctional SGs can be accomplished by restricting blood flow to the one or more dysfunctional SGs and the environment of the one or more dysfunctional SGs, or inducing HIFs in the SG.

The restricting of the blood flow may be accomplished by contracting or closing one or more blood vessels around the one or more dysfunctional SGs by using one or more of a pharmaceutical, surgery, a laser, an intense pulsed light, and a device.

Therefore, considering the important role of SG in promoting health of hair follicles, one embodiment of the present disclosure is directed to a method of treating hair loss, occurring due to SGD. This may again be accomplished by reducing oxygen concentration in an environment of one or more dysfunctional SGs, thereby restoring a hypoxic status of the environment of the one or more dysfunctional SGs or by inducing HIFs in the SG.

Therapeutic techniques and methods disclosed for treating MGD or SGD, in accordance to embodiments of the present disclosure, involve decreasing oxygen delivery to the affected MGs and SGs. The approaches which can be applied for decreasing oxygen delivery can be one or more of pharmaceutical (e.g. drugs), surgical (e.g. laser or intense-pulsed light) and/or device-mediated (e.g. hypoxia chamber goggle for MGD). In addition, these approaches could be any safe and effective method to restore a relatively hypoxic environment for the MGs and SGs, and could entail methods to constrict or close blood vessels (in order to restrict the blood flow) in the vicinity of the MGs or SG or inducing HIFs in MGs or SGs.

Restricting blood flow may be achieved for example using one or more of a 532-nm potassium titanyl phosphate (KTP) laser, a 532-nm neodymium yttrium-aluminum-garnet (Nd:YAG) laser, a 578-nm copper vapor laser, 585-600-nm pulsed dye laser (PDL), a dual 595-nm PDL, a long-pulse alexandrite (755 nm), a 800-983-nm diode laser, a 1,064-nm Nd:YAG laser, indocyanine green augmented laser therapy, PDL treatment combined with rapamycin, intense pulsed light (IPL), carbon dioxide ($CO_2$) laser, cryotherapy, vascular endothelial growth factor (VEGF)/vascular endothelial growth factor receptor (VEGFR) inhibitors or antagonists, systemic and/or local beta-blockers, anti-angiogenic molecules and mixtures thereof, as well as other approached of limiting or reducing the oxygen concentration in and around a targeted tissue site such as one or more dysfunctional MGs and the eye lid environment of one or more dysfunctional MGs.

Inducing HIFs may be achieved for example by using one or more of the hypoxia mimetic agents, such as prolyl hydroxylases inhibitors, (i.e. FG-4592/roxadustat, FG-2216, daprodustat/GSK1278863, vadadustat/AKB-6548, molidustat/BAY 85-3934, desidustat/ZYAN1), Dimethyloxalylglycine (DMOG), desferrioxamine (DFX) and cobalt chloride (CoCl2) systemically, topically or locally.

We claim:

1. A method of treating meibomian gland dysfunction, the method comprising:
   identifying loss of hypoxic status in an eyelid environment of a patient; and
   reducing oxygen concentration or inducing hypoxia-inducible factors in said eyelid environment of one or more dysfunctional meibomian glands, thereby restoring a hypoxic status of the eyelid environment or stimulating hypoxia-related pathways in the one or more dysfunctional meibomian glands,
   wherein the reducing of the oxygen concentration is accomplished by restricting blood flow to the one or more dysfunctional meibomian glands and the eyelid environment of one or more dysfunctional meibomian glands, and
   wherein restricting the blood flow consists essentially of application of a 532-nm potassium titanyl phosphate (KTP) laser, a 532-nm neodymium yttrium-aluminum-garnet (Nd:YAG) laser, a 578-nm copper vapor laser, 585-600-nm pulsed dye laser (PDL), a dual 595-nm PDL, a long-pulse alexandrite (755 nm), a 800-983-nm diode laser, a 1,064-nm Nd:YAG laser, or indocyanine green augmented laser therapy.

2. The method of claim 1, wherein the restricting of the blood flow is accomplished by contracting or closing one or more blood vessels around the one or more dysfunctional meibomian glands.

3. The method of claim 1, wherein the hypoxic status is induced pharmaceutically.

4. The method of claim 1, wherein the hypoxic status is induced surgically.

5. A method of treating meibomian gland dysfunction, the method comprising:
   identifying loss of hypoxic status in an eyelid environment of a patient; and
   reducing oxygen concentration or inducing hypoxia-inducible factors in aft said eyelid environment of one or more dysfunctional meibomian glands, thereby restoring a hypoxic status of the eyelid environment or stimulating hypoxia-related pathways in the one or more dysfunctional meibomian glands,
wherein the reducing of the oxygen concentration is accomplished by restricting blood flow to the one or more dysfunctional meibomian glands and the eyelid environment of one or more dysfunctional meibomian glands,
wherein restricting the blood flow is achieved using one or more of a 532-nm potassium titanyl phosphate (KTP) laser, a 532-nm neodymium yttrium-aluminum-garnet (Nd:YAG) laser, a 578-nm copper vapor laser, 585-600-nm pulsed dye laser (PDL), a dual 595-nm PDL, a long-pulse alexandrite (755 nm), a 800-983-nm diode laser, a 1,064-nm Nd:YAG laser, indocyanine green augmented laser therapy, PDL treatment combined with rapamycin, intense pulsed light (IPL), carbon dioxide ($CO_2$) laser, cryotherapy, vascular endothelial growth factor (VEGF)/vascular endothelial growth factor receptor (VEGFR) inhibitors or antagonists, systemic and/or local beta-blockers, anti-angiogenic molecules and mixtures thereof, and
wherein the hypoxic status is induced using an intense-pulsed light.

6. The method of claim 1, wherein the hypoxic status is induced with a device.

7. The method of claim 1, wherein the hypoxic status is induced using hypoxia chamber goggles.

8. The method of claim 3, wherein the hypoxic status is induced by prolyl hydroxylases inhibitors, Dimethyloxalylglycine (DMOG), desferrioxamine (DFX) or cobalt chloride ($CoCl_2$).

9. The method of claim 8, wherein the prolyl hydroxylases inhibitors comprise one or more of FG-4592/roxadustat, FG-2216, daprodustat/GSK1278863, vadadustat/AKB-6548, molidustat/BAY 85-3934, and desidustat/ZYAN1.

10. The method of claim 1, wherein telangiectasia of said eyelid is identified in said patient.

* * * * *

UNITED STATES PATENT AND TRADEMARK OFFICE
CERTIFICATE OF CORRECTION

PATENT NO. : 11,554,048 B2
APPLICATION NO. : 16/289195
DATED : January 17, 2023
INVENTOR(S) : David A. Sullivan and Yang Liu It is certified that error appears in the above-identified patent and that said Letters Patent is hereby corrected as shown below:

On the Title Page

Column 2 (Item (57) Abstract), Line 9, after "meibomian" insert -- and --

In the Claims

In Column 8, Line 61, Claim 5, after "in" delete "aft"

Signed and Sealed this
Twenty-third Day of January, 2024

Katherine Kelly Vidal
*Director of the United States Patent and Trademark Office*